United States Patent
Aoyagi et al.

(10) Patent No.: US 7,257,871 B2
(45) Date of Patent: Aug. 21, 2007

(54) DEAD HUMAN BODY EMBALMING METHOD

(75) Inventors: Kohei Aoyagi, Chuo-ku (JP); Yoshinobu Sato, Shibuya-ku (JP); Shinichiro Ishida, Nagoya (JP)

(73) Assignees: Kabushiki Kaisha Sunseal, Osaka-shi (JP); Asukatec Co., Ltd., Iwakura-shi (JP); Yoshinobu Sato, Shibuya-ku (JP); San Holdings Inc., Osaka-shi (JP)

( * ) Notice: Subject to any disclaimer, the term of this patent is extended or adjusted under 35 U.S.C. 154(b) by 41 days.

(21) Appl. No.: 11/240,053

(22) Filed: Sep. 30, 2005

(65) Prior Publication Data

US 2007/0044288 A1    Mar. 1, 2007

(51) Int. Cl.
*A61G 17/00* (2006.01)

(52) U.S. Cl. .............................. 27/11; 27/22.1; 27/22.2; 27/23.1; 27/24.1

(58) Field of Classification Search .................... 27/11, 27/22.1, 22.2, 23.1, 24.1
See application file for complete search history.

(56) References Cited

U.S. PATENT DOCUMENTS 4,351,091 A * 9/1982 Goodkin ...................... 27/22.1
5,216,789 A * 6/1993 Pomares et al. ............. 27/22.1

FOREIGN PATENT DOCUMENTS

JP        06-024901        2/1994

OTHER PUBLICATIONS

Robertine Frederick, The Principles and Practice of Embalming, 1989, Fifth Edition, Professional Training Schools, Inc., Dallas, TX.

* cited by examiner

*Primary Examiner*—Jacqueline F. Stephens
(74) *Attorney, Agent, or Firm*—Pitney Hardin LLP

(57) ABSTRACT

According to the present invention, for a dead human body in which the blood contains a predetermined ratio or more of bilirubin, which causes discoloration of the body, before the primary embalmment processing employing the perfusion type antiseptic fixing method using a formalin solution, the body is cleaned with an antiseptic solution, and the preliminary processing is performed. Specifically, a photo catalyst embalming solution containing a photo catalyst is injected into the vessels of the body, and after the photo catalyst embalming solution has been distributed to the capillaries in the dermis of portions of the body for which discoloration is to be prevented, the portions are irradiated by an electromagnetic wave (e.g., UV) to induce photo catalytic activity to locally, at the least, decompose bilirubin and reduce the amount in the body portions. As a result, the appearance of a body in a special state, wherein the amount of bilirubin is excessive, can be maintained so it is as natural as possible.

14 Claims, 3 Drawing Sheets

DEAD HUMAN BODY EMBALMING METHOD

BACKGROUND OF THE INVENTION

1. Field of the Invention

The present invention relates to a dead human body embalming method for preventing decomposition and for preserving human bodies for which death was the result of various causes.

2. Related Arts

Since for human bodies, for which death was the result of various causes, tissue degeneration and damage proceed quickly, discoloring the skin and producing odors and gas, bodies of the dead are conventionally cleaned using an antiseptic solution, such as ethanol, and are cooled with dry ice or with an ice bag to delay decomposition. But, while disinfection of the skin surface and cooling applied from the outside can, to a degree, delay decomposition, this processing method is not very effective during a hot summer or in a location having a warm or tropical climate. Further, since when such a cooling preservation method is used the surface of a body is rapidly cooled and the skin is darkened, the appearance of the body tends to become even more unnatural.

Furthermore, since embalmment and sterilization of the organs of a body are not possible when ethanol, formalin or another antiseptic solution is used only for surface disinfection, internally retained viruses and other pathogenic bacteria can be discharged with the gas generated by decomposition, and medical personnel and bereaved family members, and those other than the immediate family who attend a funeral service, may be in danger of contracting an infectious disease. Aside from the process that has been described here, there is one old anatomic preservation method whereby, for the antiseptic processing of a deceased, the body is immersed in a formalin solution of about 5 to 7% and the formalin is permitted to permeate the skin. However, as it has elsewhere been pointed out, this is not an acceptable method because a long, drawn-out procedure is required, since a protracted period is required for the formalin to permeate the surface of skin, and also because this method can not satisfactorily prevent the spread of infectious diseases. There is, however, another popular antiseptic and bacteriological fixing method, currently used for anatomical preservation, for which a perfusion type fixing procedure is employed that includes the injection of an antiseptic fixing solution into an artery of a body and the discharge of blood from a vein.

This type of anatomical preservation procedure is generally called "embalming". Embalming not only tends to preserve and improve the external appearance of a body, thereby reducing the disturbing effect viewing the body could have on a bereaved family and other mourners at a funeral, but also normally resolves the problems attendant with the spread of an infectious disease, and unhygienic conditions. Embalming, therefore, is performed for 90 to 95% of the dead in North America, in the United States and Canada, 70 to 75% of the dead in The United Kingdom and Northern Europe, and 70% of the dead in Singapore, and its use in Japan is gradually increasing.

One conventional embalming example using the perfusion type of antiseptic fixing method is disclosed in Japanese Unexamined Patent Publication No. Hei 6-24901. According to this embalming method, incisions are made in a body in at least two places, and a preservative agent is injected, by manual injection hand pump, through a blood vessel (e.g., a femoral artery) at one of the incisions, and this injected agent forces blood out, discharging it from another vessel (e.g., a carotid artery) at the other incision. In this manner, the blood inside a body can be replaced with the agent, and the body preserved while not distorting its external shape. Agents that can be used for this embalmment procedure are also disclosed.

According to this publication, for injection, a liquid agent is required that has an antimicrobial or an antiseptic function. Formalin, cresol, phenol or isopropanol may be employed, although a formalin solution or a formalin and phenol solution having a density of 40% or less is preferable. Furthermore, according to this publication, since the contents of the abdominal organs, such as the stomach and intestines, are aspirated, defects such as decomposition and discoloration do not occur before thirty days have elapsed. As described above, embalming wherein formalin is used for disinfection and preservation provides appropriate effects.

However, when because of impaired liver function, for example, the blood in a dead body contains a predetermined level or higher of bilirubin, which is the main element of a bile pigment, and signs of jaundice have appeared on the body, the color of the body changes to green, due to a chemical reaction with the formalin element. It is said that of all dead bodies, the number for which symptoms of jaundice are present can reach about 10%. When such discoloration occurs in the capillaries in the dermis, the skin of the body turns green, and the appearance is far removed from that of living tissue. This is absolutely not desirable because it would shock the bereaved family and other people who viewed the body. Therefore, When such discoloration does occur, a conventional, temporary measure used to hide the green skin is the application to the body of a thick, unnatural make-up.

SUMMARY OF THE INVENTION

One objective of the present invention is to provide a body embalming method whereby, before the perfusion type antiseptic fixing method is employed for the prevention of decomposition and embalmment of a dead human body in a special state, wherein the blood contains an excessive amount of bilirubin, the amount of bilirubin is reduced to ensure that once the procedure has been completed, the body has as natural an appearance as possible.

According to a first aspect of the present invention, a body embalming method is provided whereby, for the embalmment of a body that it has been ascertained contains a predetermined ratio or more of bilirubin, which can cause discoloration of the skin, incisions in the body are made in at least two locations, a preservative solution containing a formalin element is injected, using a pump, through a blood vessel at one of the incisions and, through the injection of the preservative solution, blood is discharged from a blood vessel at the other incision to replace the blood in the body with the preservative solution and to maintain the external shape of the body while the body is being embalmed, there is performed, prior to the performance of a primary process for the perfusion type antiseptic fixing method for embalming a body, a preliminary process:

for cleaning the body using an antiseptic solution;

for injecting, into vessels in the body, a photo catalyst embalming solution that contains a photo catalytic material;

for, after adequate time has elapsed for the photo catalyst embalming solution to have been dispersed to capillaries in the dermis of body portions whereat discoloration is to be prevented, using an electromagnetic wave, such as an ultraviolet ray, to irradiate the body portions to excite electrons of the photo catalytic material and generate photo catalytic activity, and for locally, at least, decomposing and reducing bilirubin. "Electromagnetic wave" means, in general, "radiation" that can effectively generate photo catalytic activity through irradiation of the photo catalytic material, and as a concept, includes independent ultraviolet radiation having a specific wavelength range, radiation for which ultraviolet rays having different wavelength ranges are superimposed, and radiation for which visible light is partially superimposed on ultraviolet light. Preferable radiation intensity should be determined in accordance with the type and properties of the photo catalyst that is to be irradiated.

According to a second aspect of the invention, for the body embalming method, a bilirubin content for which the preliminary process is required is determined, at the least, in accordance with when symptoms of jaundice are confirmed or in accordance with the results of a blood test.

According to a third aspect of the invention, for the body embalming method, body portions whereat discoloration is to be prevented include, at the least, the face, the head and both hands.

According to a fourth aspect of the invention, for the body embalming method, especially for increasing photo catalytic activity, a photo catalytic material solution in which fine-grained metal is suspended is employed as the photo catalyst embalming solution, and the density of the photo catalytic material solution in which the fine-grained metal is suspended is 0.3 to 10%.

According to a fifth aspect of the invention, for the body embalming method, especially for increasing the photo catalytic action, a photo catalytic material solution in which fine-grained metal is suspended is employed as the photo catalyst embalming solution, and the density of the photo catalytic material solution in which the holding fine-grained metal is suspended is 0.5 to 5%.

According to a sixth aspect of the invention, for the body embalming method, the diameter of fine grains of the photo catalytic material selected for the photo catalyst embalming solution is equal to or smaller than 1 μm.

According to a seventh aspect of the invention, for the body embalming method, the photo catalyst embalming solution contains an organic medicine element in addition to the fine grains of photo catalytic material.

According to an eighth aspect of the invention, for the body embalming method, the photo catalytic material selected is a photo catalytic activity capable metal oxide semiconductor, such as titanium oxide, zinc oxide, tungstic oxide, cadmium sulfide or a visible light response photo catalyst, or a metallic sulfide. In this case, as in a ninth aspect of the invention, it is preferable that a metal oxide semiconductor providing high oxidization, high reduction, high stability and high safety be selected as the photo catalytic material; a titanium oxide semiconductor is especially preferable. It is further preferable that titanium oxide, which is a photo catalytic material, be employed alone or in combination with multiple light sources selected from among anatase titanium oxide, rutile titanium oxide, strontium titanate and visible light response titanium oxide, for which metallic ions are included and for which an impurity level smaller than a band gap inherent to titanium oxide is applied that permits the use of visible light.

According to a tenth aspect of the invention, for the body embalming method, an electromagnetic wave used to generate the photo catalytic activity is equal to or shorter than a wavelength in a visible light region, for example, that is equal to or smaller than a wavelength of 600 nm.

According to an eleventh aspect of the invention, for the body embalming method, one irradiation source, or a combination of irradiation sources, is selected from among a group including an HID lamp, a fluorescent tube, a cold-cathode discharge tube and an LED and is used as a light source for electromagnetic wave irradiation.

In this case, electromagnetic wave means radiation that can apply photo energy corresponding to a band gap unique to the photo catalytic material and that can excite the electrons of the photo catalytic material to a conduction band. Therefore, the above described irradiation sources that cover the range from ultraviolet light to visible light is effective. Especially when titanium oxide, such as anatase titanium, rutile titanium or strontium titanate, is employed, a wavelength equal to or shorter than 600 nm is necessary. When a dispersed precious metal is employed as a transient metal element, in particular, as in a photo catalytic material (product of Asukatec Co., Ltd.), wherein fine silver grains are dispersed, a wavelength equal to or shorter than 387 nm is required relative to titanium dioxide.

According to the body embalming method of the invention, during embalmment performed using the perfusion antiseptic fixing method, for which a formalin solution is employed for a body for which the symptoms of jaundice have appeared because a predetermined amount or more of bilirubin, which can cause bodily discoloration, is contained in the blood, a preliminary process is performed first to locally decompose bilirubin in capillaries in the dermis and to reduce the bilirubin content of the blood in the capillaries. Thereafter, the primary process for the embalmment of the body is performed to prevent the body from becoming discolored and the surface from turning green.

This preliminary process is performed for a body for which it is determined the probability is high that discoloration will occur, because there are signs of jaundice or because a blood test indicated the bilirubin content was high, and for which it is desired, at the least, to locally decompose bilirubin in the capillaries of specific portions, such as the face, the head and the hands, and to reduce the bilirubin content. The organic decomposition action effected by a photo catalyst is employed to decompose bilirubin, and to reduce the density of bilirubin in the capillaries in the dermis that are near the surface of the skin.

In this invention, a photo catalyst embalming solution that contains titanium dioxide, which is one type of photo catalytic material, is injected into vessels and is distributed to capillaries. Then, ultraviolet light, which is one type of electromagnetic wave used to generate photo catalytic activity, is externally emitted to irradiate desired portions of the body. In this manner, the photo catalyst is activated to at least decompose bilirubin locally, and the density of bilirubin content is reduced until equal to or lower than the ratio at which discoloration occurs. A metal oxide semiconductor providing high oxidization, high reduction, high stability and high safety is selected as the photo catalytic material, and a titanium oxide semiconductor is especially preferable. It is preferable that titanium oxide, which is a photo catalytic material, be employed alone or as one of a combination of multiple light sources selected from among anatase titanium oxide, rutile titanium oxide, strontium titanate and visible light response titanium oxide, into which metallic ions are mixed and an impurity level smaller than a band gap inherent to titanium oxide is applied so as to permit the use of visible light. The diameter of each fine grain is adjusted so as to be equal to or smaller than 1 μm, which will permit it to easily enter the tip of a capillary. Further, a photo catalytic material is preferable wherein are dispersed, as a transient metal element, fine grains of a precious metal, especially silver or platinum.

Especially to increase the photo catalytic action, a photo catalytic material solution in which fine-grained metal is suspended is employed as the photo catalyst embalming solution, and the density of the photo catalytic material solution in which the fine-grained metal is suspended is 0.3 to 10%, preferably, 0.5 to 5%. Therefore, after the photo catalyst embalming solution has been injected into an artery, within a predetermined period of time, e.g., one to two hours, the solution reaches the capillary at desired portions and is irradiated by an electromagnetic wave to generate photo catalytic activity. Then, the photo catalytic fine grains are activated and bilirubin is decomposed.

The wavelength of ultraviolet light, which is an electromagnetic wave, used to generate the photo catalytic activity of the photo catalyst embalming solution is equal to or shorter than 387 nm, and the amount of ultraviolet light used to irradiate a unit area is defined as 1 $mW/cm^2$ to 10 $mW/cm^2$. As a result, an embalmment procedure can be performed whereby the photo catalytic material retained in capillaries in the dermis of the body is appropriately activated and the body is not heavily tanned. It is more convenient for the photo catalyst embalming solution to contain an organic medicine element in addition to the fine photo catalytic grains. A source for the electromagnetic wave used for the irradiation employed to generate photo catalytic activity can be one irradiation source, or a combination of multiple irradiation sources, is selected from among a group including an HID lamp, a fluorescent tube, a cold-cathode discharge tube and an LED. Actually, an appropriate type of electromagnetic wave for generating photo catalytic activity should be selected in accordance with the element used in the photo catalyst embalming solution, and the use of an electromagnetic wave that is either ultraviolet light belonging to UV-A (a wavelength of 320 to 380), to UV-B (a wavelength of 280 to 320) or to UV-C (a wavelength of 200 to 280) and is broadly divided, and depending on the wavelengths, a combination of these ultraviolet sources, or a mixture of ultraviolet light and visible light should be studied. Or not only an interrupted spectral radiation source, for which an arbitrary fluorescent discharge lamp is employed, but also a continuous spectral radiation source, for which temperature radiation is employed, can be used together for the operational principle of a radiation apparatus.

DETAILED DESCRIPTION OF THE PREFERRED EMBODIMENTS

The present invention relates to a body embalming method whereby, when the prevention of decomposition and embalmment of a dead human body is to be performed by employing the perfusion type antiseptic fixing method, the amount of bilirubin is reduced for a body in a special state, wherein the blood contains an excessive amount of bilirubin, so that the appearance of the body remains as nearly natural as possible. A body embalming method according to the preferred embodiments of the present invention will be described while referring to the accompanying drawings. However, the present invention is not limited to this embodiment.

Figure 1:
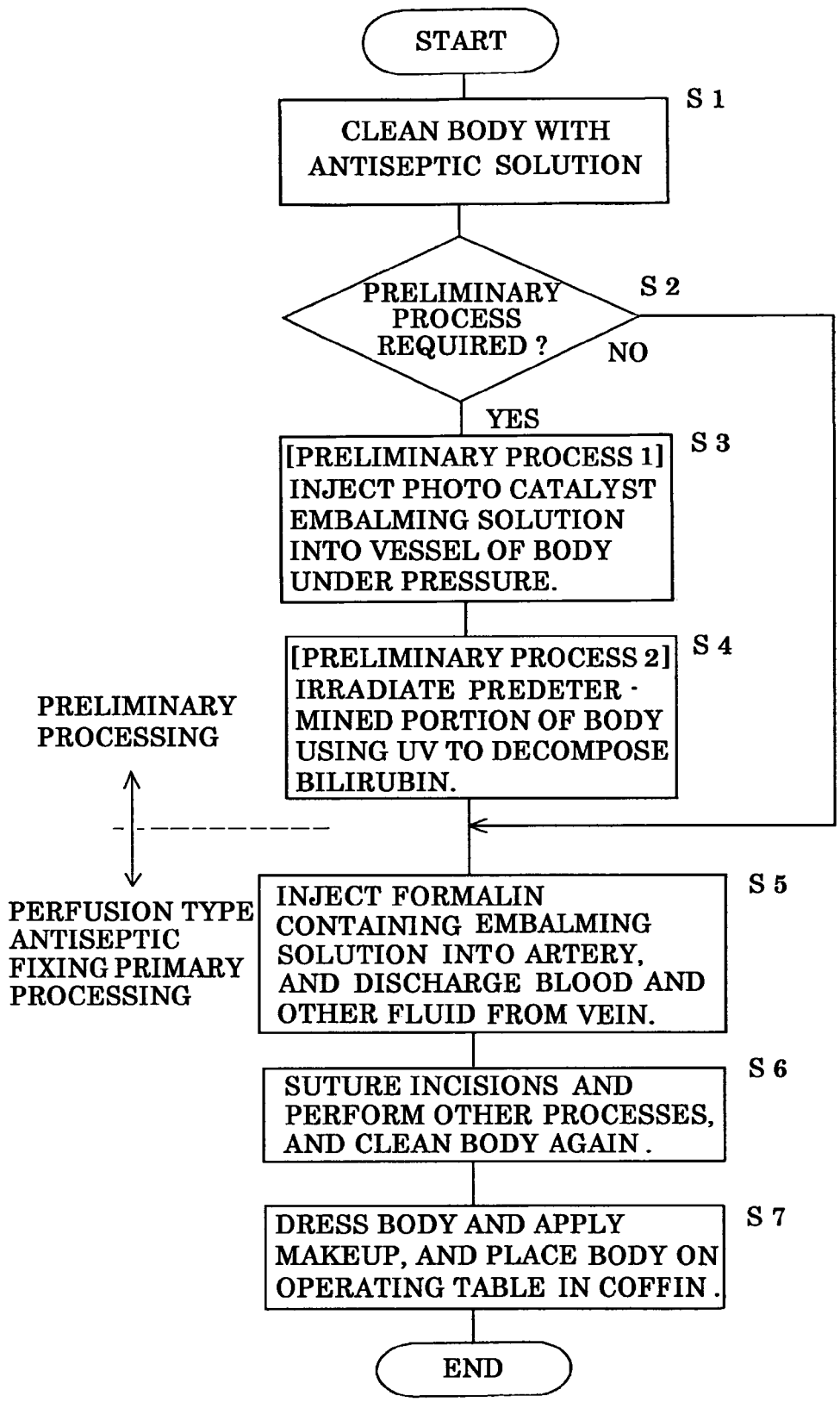
FIG. 1 is a flowchart showing the processing for a body embalming method according to the present invention.

FIG. 1 is a flowchart showing the body embalming method for employing the perfusion type antiseptic fixing procedure and a photo catalyst embalming solution according to the present invention. Before the processing is begun, a body is cleaned with an antiseptic solution, such as ethanol (step S1). Following this, before shifting to the primary processing, at step S5, for employing the perfusion type antiseptic fixing method to embalm the body, a check is performed to determine, based on the amount of bilirubin in the body, whether the preliminary processing is required (step S2).

The performance of this determination depends on whether symptoms of jaundice have appeared, or on whether, as a result of an analysis of the blood in the body, it has been determined the bilirubin content falls within or exceeds a predetermined range. When it has been determined that the preliminary processing is required, a preliminary process 1 is performed during which incisions are made in predetermined portions of the body, such as the face and the hands, and a photo catalyst embalming solution is injected under pressure (step S3). The processing is then suspended until the photo catalyst embalming solution has been distributed to the capillaries in the dermis at the predetermined portions. Thereafter, a preliminary process 2 is performed during which the predetermined portions of the body are irradiated with ultraviolet light to, at the least, locally decompose the bilirubin (step S4). This preliminary processing will be described in detail later. When, however, it is determined at step S2 that the preliminary processing is not required, the preliminary processes 1 and 2 are skipped and program control is shifted to the primary processing for which the perfusion type antiseptic fixing method is employed.

When the preliminary processes 1 and 2 have been completed or when it has been determined that the preliminary processing is not required, the perfusion type antiseptic fixing method is employed to inject a formalin solution into arteries, using a pump, and to discharge blood from veins (step S5). When the preliminary processing at steps S3 and S4 has been performed, the photo catalyst embalming solution and blood are mixed together and the two are discharged at the same time. The injection process is terminated when the formalin solution has been distributed to all interior parts of the body.

When the injection process has been completed, the incised portions are sutured and the entire body is again cleaned (step S6). Thereafter, the body is dressed, covering makeup is applied, as necessary, to the face, and the body is either mounted on an operating table or placed in a coffin. Thus, the embalming processing is terminated (step S7).

During an embalming process that employs the perfusion type antiseptic fixing method, and that includes the preliminary processing and the primary processing described above, the basic procedure comprises components of the primary processing, whereby blood in a body is locally, at the least, replaced by a formalin solution, performed in accordance with a known conventional embalming method for employing the perfusion type antiseptic fixing method.

When, however, a body contains a predetermined amount or more of the bilirubin that can cause skin discoloration, conventionally, a phenomenon involving a chemical reaction, in the capillaries of the skin (dermis), that turns the skin of a body green can not be coped with, and only after-the-event measures, i.e., the covering of affected skin areas with a thick, unnatural makeup, can be taken. According to the invention, however, during the additionally provided preliminary processing, a basic measure is taken to reduce the bilirubin content of the blood in the vessels of a body, i.e., a chemical reaction is induced to decompose, to the extent possible, the bilirubin that can cause discoloration of the body.

The preliminary processing corresponding to the essential portion of the present invention will now be described. A metal oxide semiconductor capable of high oxidization, high reduction, high stability and high safety is selected as a photo catalytic material to be suspended in a photo catalyst embalming solution, and for this, a titanium oxide semiconductor is especially preferable. It is furthermore preferable that titanium oxide, which is a photo catalytic material, be employed alone or as one of a combination of multiple light sources selected from among anatase titanium oxide, rutile titanium oxide, strontium titanate and visible light response titanium oxide, into which metallic ions are mixed and an impurity level smaller than a band gap inherent to titanium oxide is applied so as to permit the use of visible light. Furthermore, a photo catalytic material solution in which are suspended, as a transient metal element, fine grains of a precious metal, especially silver or platinum, is preferable as a photo catalyst embalming solution. The density of the photo catalytic material in the photo catalyst embalming solution is determined within a range such that the bilirubin decomposition period is not too long and takes about two hours. The photo catalyst embalming solution can appropriately contain another organic material. Especially, for a conventional embalming solution that contains a formalin solution, an element can be added that prevents the coagulation of blood and improves flowability, facilitating injection.

When it is determined that the preliminary processing is required, as well as the primary processing in the conventional embalming processing, incisions are made at appropriate portions, such as the neck or a thigh, in a body that has been completely cleaned using an antiseptic solution, such as ethanol, and the photo catalyst embalming solution of this composition is injected into an artery, under pressure applied by using a pump, until it is distributed to the capillaries in the dermis. The amount of the photo catalyst embalming solution that is injected is determined while taking into account, for example, the sex, the age and the size of a body, and the content level of the bilirubin in the blood. After the injection procedure has been performed, further processing is suspended until the photo catalyst embalming solution has reached the capillaries of the face, the head or a hand, for example, and while waiting until irradiation has been performed using an appropriate electromagnetic wave, such as ultraviolet light or a mixture of ultraviolet light and visible light, to induce photo catalytic activity in the photo catalytic material that has been injected.

Figure 2:
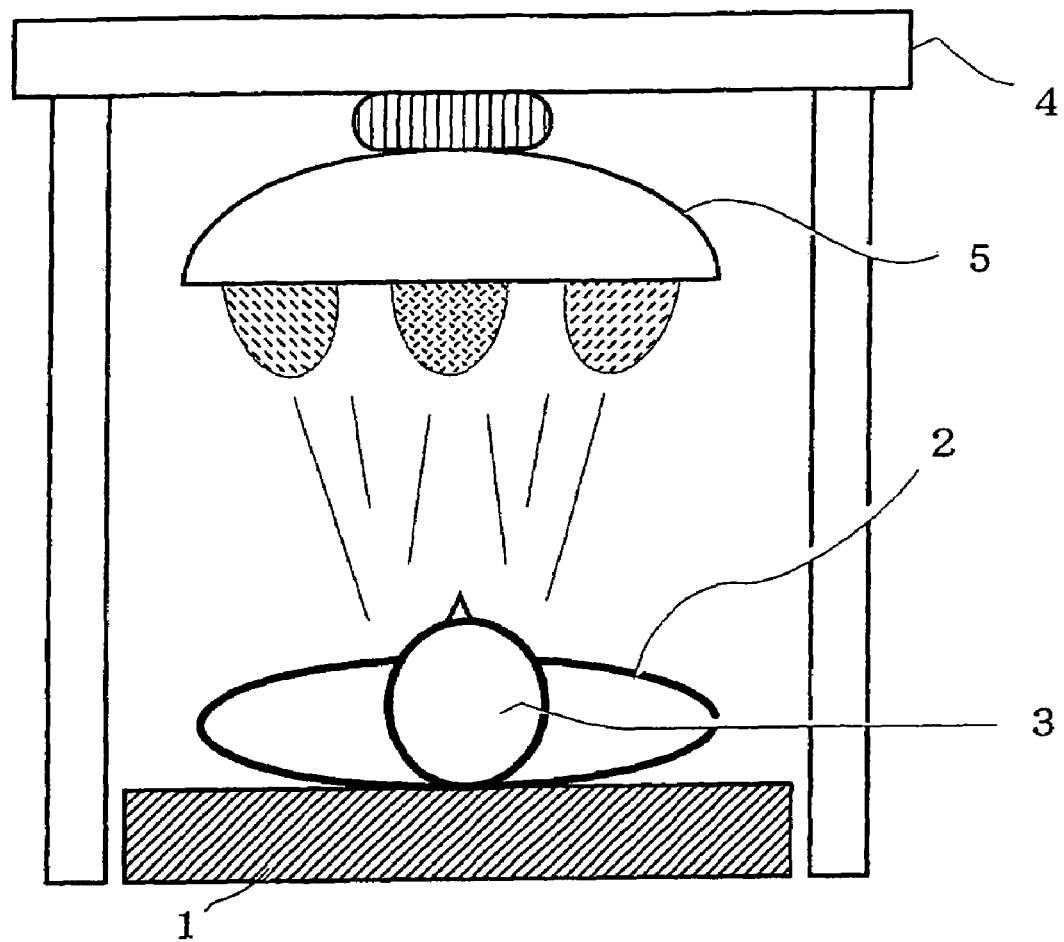
FIG. 2 is a conceptual diagram showing the arrangement for electromagnetic wave irradiation according to one embodiment of the present invention.

Various patterns can be employed for an irradiation apparatus, such as an ultraviolet irradiation apparatus, to generate an electromagnetic wave for inducing photo catalytic activity in a predetermined portion of a body. For example, as shown in FIG. 2, the face and a head 3 of a body 2 placed on an operating table 1 is irradiated by an ultraviolet irradiation apparatus 5 that is attached to a frame 4 located above the head 3. From the viewpoint of the irradiation efficiency, it is preferable that special small ultraviolet irradiation apparatuses for "hands" be arranged to separately irradiate both hands (not shown), which are placed on the chest. The irradiation source of the electromagnetic wave (e.g., UV) irradiation apparatus 5 can, for example, be a UV lamp that generates ultraviolet light having a wavelength near 360 nm, a UV discharge tube or a UV LED; however, any arbitrary irradiation source can be employed.

While taking into account the fact that since a face is a three dimensional figure and at the tip of the nose and the ears, as elsewhere, there are considerable undulations and raised and recessed portions, consideration must be given to obtaining and using a reflection cover having an appropriate shape, so as to reduce the processing time, and to providing adequate coverage for a face by moving and pivoting the irradiation source, as time elapses, along a curved guide rail. Further, multiple UV LEDs may be arranged on the internal wall of the reflection cover at the head, and a distal output portion, to which the output of a strong UV discharge lamp is guided along multiple optical fibers, may be arranged on the internal wall of a mask-like cover that is located at an appropriate interval from the face. With this arrangement, UV can be projected at close range. In any case, however, it is preferable that local tanning or uneven tanning be avoided.

Embodiment 1

As the photo catalyst embalming solution used for the body embalming method described above, the following solution is effective: a photo catalytic material (product of Asukatec Co., Ltd.), wherein fine grains of a transient precious metal element, especially silver, are held suspended in a titanium dioxide ($TiO_2$) solution. Since the diameter of the fine grains of silver that are suspended in the titanium dioxide ($TiO_2$) solution is about 100 nm, these grains can easily be distributed to and pass through capillaries in the dermis.

Figure 3:
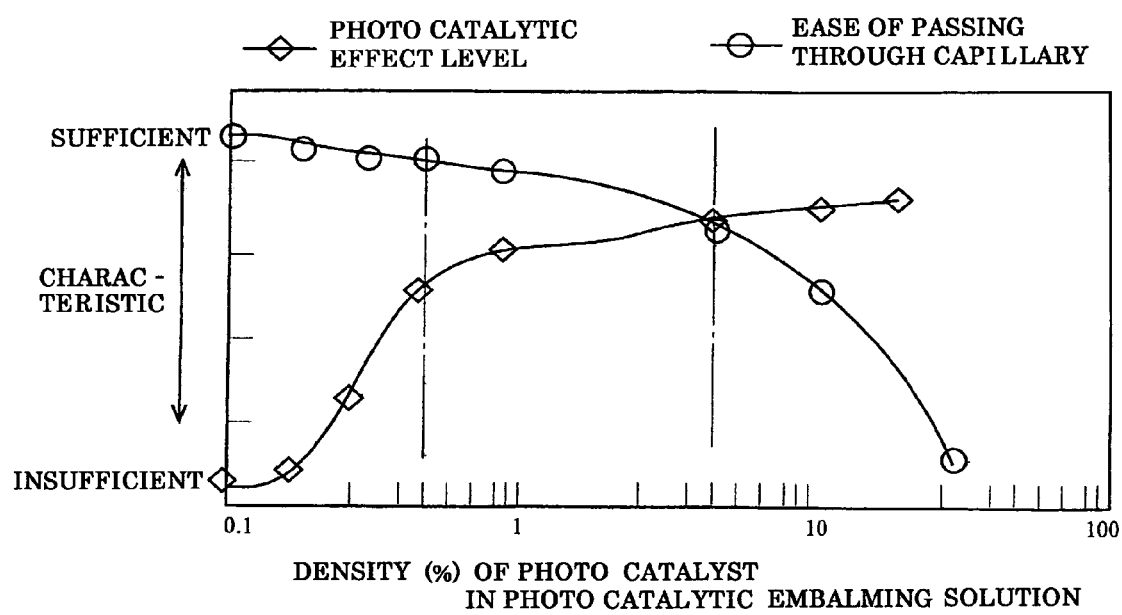
FIG. 3 is a graph showing a correlation between the property of a photo catalyst embalming solution and a photo catalytic action.

FIG. 3 is a graph showing the correlation between how easily the photo catalyst embalming solution can pass through capillaries (curve with added circles) and the satisfaction level (curve with added rhombi) attained by the induced photo catalytic activity, while the horizontal axis represents the density of the photo catalytic element in the photo catalyst embalming solution. The passage level illustrated for the capillaries (curve with added circles) is preferable when the density of the photo catalytic material is low. However, when the density is 5% or greater, passage through the capillaries is difficult, and when the density of the photo catalytic material exceeds 10%, the passage level drops drastically. On the other hand, the photo catalytic activity (curve with added rhombi) is gradually increased at a photo catalytic material density of about 0.2%, shows satisfactory effects at a density of 0.4 or greater, and is gradually saturated. While taking these two curves into account, the density of the photo catalytic material is preferably 0.3 to 10%, and more preferably 0.4 to 5%. In this case, a UV lamp that emitted ultraviolet light having a wavelength near 360 nm was employed as the irradiation source for the electromagnetic wave irradiation apparatus.

Embodiment 2

Tables 1 and 2 show relationships between ultraviolet (UV) irradiation volume and change periods at a photo catalytic material (product of Asukatec Co., Ltd.) density of 0.5% and at a photo catalytic material density of 5%. The evaluations in these tables of the decoloration effects relative to bilirubin color are categorized as follows.

0: no effects

1: thinner than the original bilirubin color

2: obviously thinner

3: obviously thinner; but still identifiable as a bilirubin color

4: decolorized and barely identifiable as a bilirubin color

X: only a tan color produced by ultraviolet light identified

[Table 1]

[Table 2]

In tables 1 and 2, 0 to 2, which indicate that the decolorization effects are regarded as unsatisfactory, are entered in shaded portions. Entered in white portions are evaluations "3" and "4", which indicate that satisfactory effects were obtained, and these are regarded as effective ranges. Further, a state wherein the decoloration effects are satisfactory but it was determined the skin of a body would be tanned by ultraviolet light is indicated by an "X". In accordance with the tables, when the density of the photo catalyst element is 0.5%, the processing time is 90 to 120 minutes when a UV irradiation of 2 to 3 mW/cm$^2$ is used, and when the density of the photo catalyst element is 5%, the processing time is 60 to 120 minutes when a UV irradiation of 2 to 3 mW/cm$^2$ is used. Therefore, correlation of not only the UV irradiation but also the irradiation time is shown, and should be appropriately adjusted in accordance, for example, with the size, the sex and the age of the body and the bilirubin content.

The body embalming method of the present invention is broadly related to the body embalming method that uses the perfusion type antiseptic fixing method. The invention especially aims at the reduction of bilirubin to a predetermined level or lower by induced photo catalytic activity, and the injection of a formalin solution that will prevent the occurrence of a phenomenon that causes a body to turn green when a large amount of bilirubin is contained in the blood, because of impaired liver function, and acts on a formalin element. Therefore, for a body that contains a large amount of bilirubin, discoloration of the face, the head and the hands, for which the preliminary processing of the invention is performed, can be avoided. Thus, an uncomfortable feeling, or shock, experienced by a bereaved family and other people who attend a funeral can be considerably reduced, and a peaceful, quiet final parting can be provided.

Various other modes of carrying out the invention are contemplated that are within the scope of the following claims that in particular point out and distinctly describe the subject matter regarded as the invention.

TABLE 1

[PHOTO CATALYST ELEMENT: 0.5%]

| TIME (MIN.) UV IRRADIATION [mW/cm$^2$] | 30 | 60 | 90 | 120 |
|---|---|---|---|---|
| 0.5 | 0 | 0 | 0 | 1 |
| 1 | 0 | 1 | 1 | 2 |
| 2 | 1 | 1 | 2 | 3 |
| 3 | 1 | 2 | 3 | 3 |
| 5 | 2 | 3 | X | X |
| 10 | 3 | X | X | X |

TABLE 2

[PHOTO CATALYST ELEMENT: 5%]

| TIME (MIN.) UV IRRADIATION [mW/cm$^2$] | 30 | 60 | 90 | 120 |
|---|---|---|---|---|
| 0.5 | 0 | 1 | 1 | 2 |
| 1 | 1 | 2 | 3 | 3 |
| 2 | 1 | 2 | 4 | 4 |
| 3 | 2 | 3 | 4 | 4 |
| 5 | 3 | 4 | X | X |
| 10 | 4 | X | X | X |

What is claimed is:

1. A method of embalming a dead human body containing at least a predetermined ratio of bilirubin comprising the steps of:

cleaning the body using an antiseptic solution;

injecting into the body a photo catalyst embalming solution that contains a photo catalytic material;

irradiating the body with an electromagnetic wave to excite electrons of the photo catalytic material and generate photo catalytic activity thereby reducing the bilirubin ratio.

2. The method of claim 1, wherein the electromagnetic wave is an ultraviolet ray.

3. The method of claim 1, wherein the body is irradiated after the photo catalyst embalming solution has been dispersed through dermis capillaries in parts of the body where discoloration is to be prevented.

4. The method of claim 3, wherein the discoloration to be prevented occurs in the body parts comprising face, head and hands.

5. The method of claim 1, wherein the bilirubin content is determined in accordance with confirmation of symptoms of jaundice or in accordance with blood test results.

6. The method of claim 1, wherein the photo catalytic material in the photo catalyst embalming solution has a density of about 0.3% to about 10%.

7. The method of claim 1, wherein the photo catalytic material in the photo catalyst embalming solution has a density of about 0.5 to about 5%.

8. The method of claim 1, wherein the photo catalytic material in the photo catalyst embalming solution contains fine grains having a diameter of at most about 1 μm.

9. The method of claim 8, wherein the photo catalyst embalming solution contains an organic medicine element.

10. The method of claim 1, wherein the photo catalytic material is selected from the group consisting of a metal oxide semiconductor and a metallic sulfide.

11. The method of claim 10, wherein the metal oxide semiconductor provides high oxidization, high reduction, high stability and high safety.

12. The method of claim 1, wherein the electromagnetic wave used to generate the photo catalytic activity is equal to or shorter than a wavelength in a visible light region.

13. The method of claim 1, wherein the irradiating of the body is accomplished with an irradiation source is selected from the group consisting of an HID lamp, a fluorescent tube, a cold-cathode discharge tube, an LED and any combination thereof.

14. The method of claim 13, wherein the irradiation source is used as a light source for the electromagnetic wave irradiation.

* * * * *